United States Patent
Perego et al.

(10) Patent No.: US 8,057,620 B2
(45) Date of Patent: Nov. 15, 2011

(54) UNIT AND A METHOD FOR FORMING ABSORBENT PADS USED IN NAPPIES/DIAPERS

(75) Inventors: Alberto Perego, Milan (IT); Stefano Nanni, Treviolo (IT); Matteo Piantoni, Albino (IT); Luca Aiolfi, Izano (IT)

(73) Assignee: GDM S.p.A. (IT)

( * ) Notice: Subject to any disclaimer, the term of this patent is extended or adjusted under 35 U.S.C. 154(b) by 458 days.

(21) Appl. No.: 11/991,642

(22) PCT Filed: Aug. 31, 2006

(86) PCT No.: PCT/IB2006/002538
§ 371 (c)(1),
(2), (4) Date: May 5, 2009

(87) PCT Pub. No.: WO2007/029115
PCT Pub. Date: Mar. 15, 2007

(65) Prior Publication Data
US 2009/0321986 A1    Dec. 31, 2009

(30) Foreign Application Priority Data

Sep. 9, 2005 (IT) .............................. BO2005A0551

(51) Int. Cl.
*B29C 43/34* (2006.01)
(52) U.S. Cl. ........ 156/196; 156/199; 156/251; 156/516; 156/556; 156/530
(58) Field of Classification Search .................. 156/298, 156/196, 199, 221, 222, 245, 250, 251, 269, 156/324, 516, 556, 530
See application file for complete search history.

(56) References Cited

U.S. PATENT DOCUMENTS

| 4,994,053 A * | 2/1991 | Lang .............................. 604/367 |
| 2005/0109442 A1* | 5/2005 | Neubauer et al. ............ 156/62.2 |

FOREIGN PATENT DOCUMENTS

| GB | 2 286 832 A | 8/1995 |
| JP | 02 111 365 A | 4/1990 |
| JP | 02-111365 | 4/1990 |
| JP | 06-278131 | 10/1994 |
| JP | 2000-290864 | 10/2000 |
| JP | 2001-327531 | 11/2001 |
| JP | 2002516191 | 6/2002 |
| WO | 99/60964 | 12/1999 |
| WO | WO 99/60964 | 12/1999 |
| WO | WO 9960964 A1 * | 12/1999 |
| WO | 2005/072671 | 8/2005 |

* cited by examiner

*Primary Examiner* — Katarzyna Wyrozebski Lee
*Assistant Examiner* — Vishal I Patel
(74) *Attorney, Agent, or Firm* — Timothy J. Klima; Shuttleworth & Ingersoll, PLC

(57) ABSTRACT

Multilayer absorbent pads for nappy/diaper pants are manufactured on a unit (1) comprising a first device (3a) and a second device (3b) by which respective first and second layers (4a, 4b) of absorbent material (5) are taken up from two infeed stations, shaped, and transferred to two release stations. The devices (3a, 3b) are synchronized in operation, and associated by way of a transfer station (8) at which the first layer (4a) of absorbent material is joined directly to the second layer (4b), positioned selectively and with the second layer still retained by suction on the second device (3b); the two layers are thereupon compressed simultaneously to form an absorbent pad (2) that emerges from the unit as a stable, one-piece core.

19 Claims, 4 Drawing Sheets

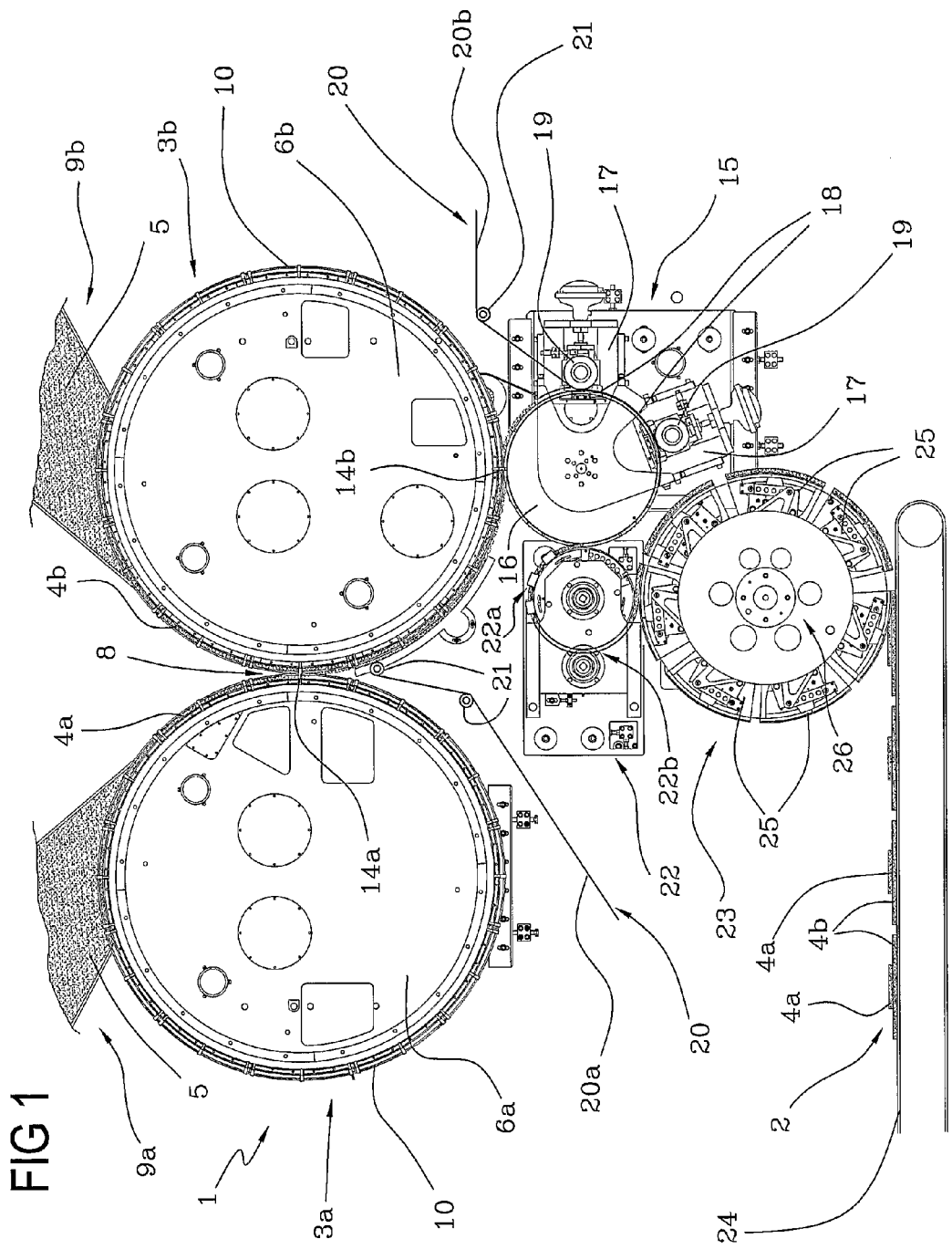

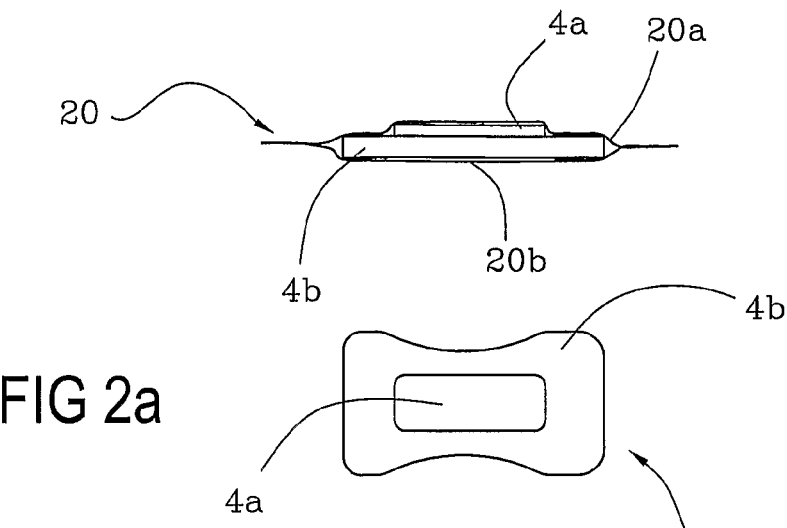
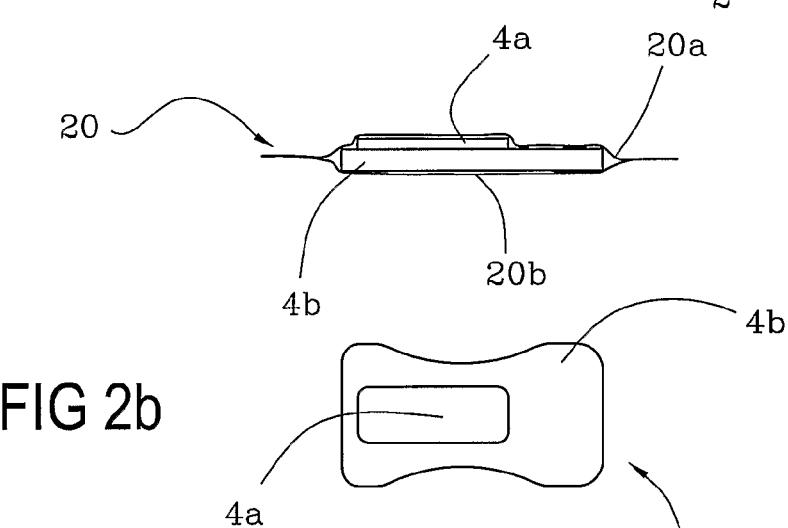
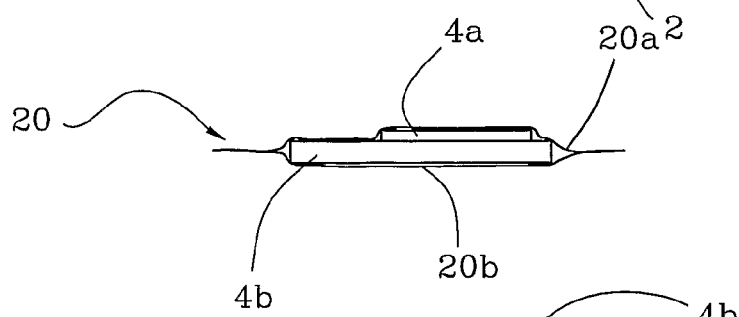
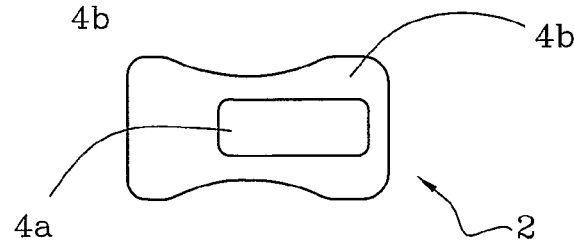

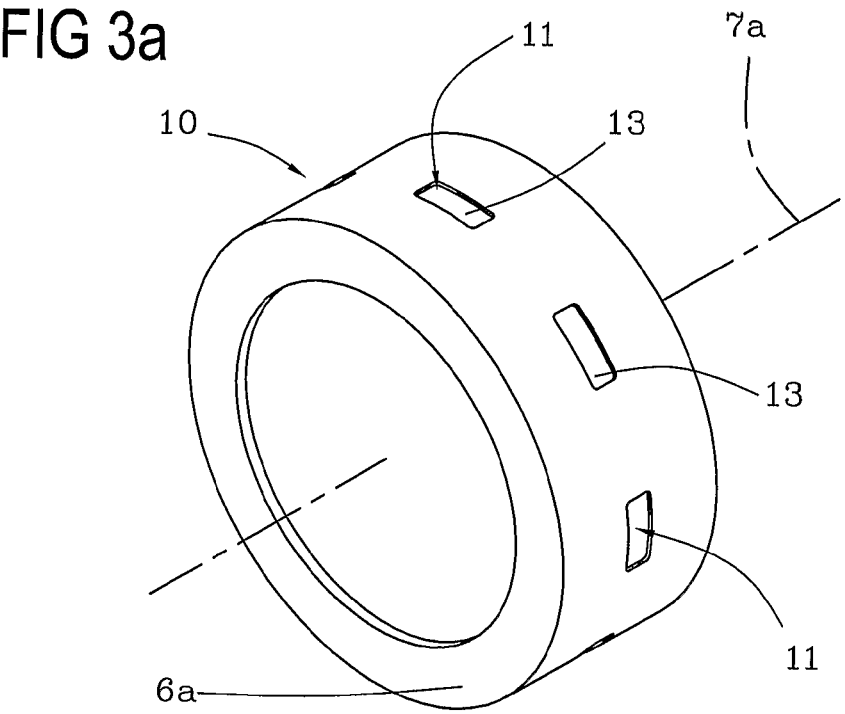
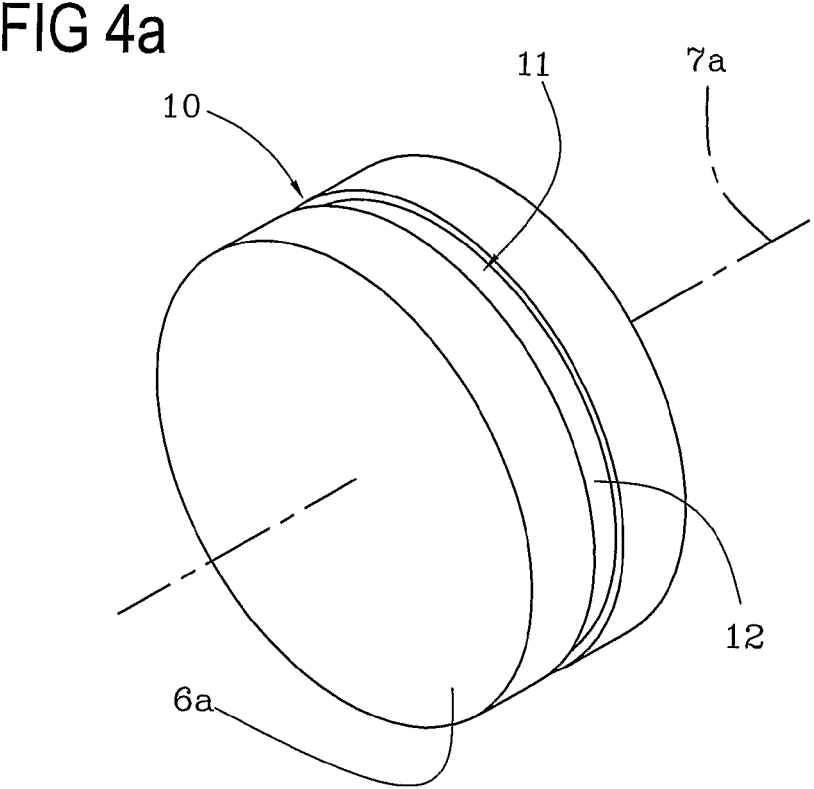

UNIT AND A METHOD FOR FORMING ABSORBENT PADS USED IN NAPPIES/DIAPERS

This application is the National Phase of International Application PCT/IB2006/002538 filed Aug. 31, 2006 which designated the U.S. and that International Application was published under PCT Article 21(2) in English.

TECHNICAL FIELD

The present invention relates to a unit and a method for forming multilayer absorbent pads as used in sanitary items.

In particular, the present invention relates to a unit of the type in question, such as can be used advantageously to fashion absorbent pads for babies' nappies/diapers.

BACKGROUND ART

A typical present-day nappy or diaper comprises an absorbent pad sandwiched normally between a permeable inner layer of spun-bonded fabric and an impermeable outer layer of polyethylene.

Responding to market demand, manufacturers of nappies/diapers now offer an anatomically contoured product, hence with pads shaped to fit a selected anatomical form. The method commonly adopted in this instance is one of forming the single pads on a drum that presents a plurality of peripheral aspirating pockets, each shaped to match the required anatomical form, and is fed at a point on the periphery with a stream of absorbent material. The absorbent material deposited in the pockets of the drum is compacted by a roller, at a point downstream.

The stream of absorbent material is a blend of cellulose pulp, or fluff pulp, into which granules of superabsorbent polymer (SAP) material are introduced either with or against the flow, homogeneously to a greater or lesser degree, according to requirements.

Nappies/diapers of more recent design also present a double thickness of absorbent padding: a first top layer, smaller, positioned on a larger second layer beneath.

In certain cases, the first layer needs also to be positioned further forward on the second layer by a greater or lesser distance in order to reinforce selected areas, depending on the gender or the age of the baby or on other factors.

Moreover, to improve the drainage of the absorbed liquid and simultaneously reduce production costs, manufacturers are opting for absorbent pads of which the composition is based on an increasingly greater quantity of SAP granules and a correspondingly smaller quantity of fluff pulp.

Adopting this new formulation, the need has also arisen for the absorbent pad to be more effectively compacted, since with a higher proportion of SAP material, which is of sand-like consistency, the structure tends to be less cohesive.

To meet the requirement for two layers of padding, the aforementioned drums present an aspirating pocket with an area of greater depth, contoured to match the shape of the finished pad. In this instance however, a special drum is needed for each relative position of the two layers, so that machines having a single drum offer scant versatility. The absorbent material can nonetheless be successfully compacted utilizing a drum of the type in question, creating a one-piece core that is easily handled and processed.

In an alternative solution, use is made of a first drum with peripheral aspirating pockets contoured to match the shape of the larger layer of padding, and a second drum adjacent to the first, set apart at a given distance, with aspirating pockets contoured to match the shape of the smaller top layer. Located beneath both of the drums is a belt conveyor, onto which the layers of absorbent material are released. The single layers are compacted by respective rollers operating between each drum and the conveyor. The larger layer is fed by the conveyor into the space beneath the second drum, from which the smaller layer is released onto the selfsame larger layer in a selected position. The timing of the two drums can be controlled in such a way as to vary the position in which the second layer is released onto the first layer. A drawback with this second solution, which envisages a first compression only of the first layer and a second compression of the second when paired with the first, is that the two layers cannot be compacted in such a way as to form a one-piece core, since the compression is applied in two successive stages, rather than simultaneously in a single step immediately before the absorbent pad is assembled with the other parts of the nappy/diaper.

The object of the present invention is to provide a unit for forming multilayer absorbent pads used in nappies/diapers, offering greater versatility than prior art units, and a method of forming such pads.

A further object of the invention is to provide a unit and a method for forming multilayer absorbent pads used in nappies/diapers whereby at least two layers of absorbent material can be suitably positioned and compacted simultaneously so as to produce a one-piece core, before the absorbent pad is assembled with the nappy/diaper pant.

DISCLOSURE OF THE INVENTION

The stated object is duly realized according to the present invention in a unit and a method for forming multilayer absorbent pads used in nappies/diapers, as recited in claims 1 and 15 or in any one of the single claims subsequent to and dependent directly or indirectly on claims 1 and 15.

The invention will now be described in detail, by way of example, with the aid of the accompanying drawings, in which:

FIG. 1 shows a preferred embodiment of a unit for forming multilayer absorbent pads used in nappies/diapers, viewed schematically in a front elevation;

FIGS. 2a, 2b and 2c are three plan views showing an absorbent pad comprising two superposed layers of absorbent material occupying three possible positions one relative to another;

FIGS. 2d, 2e and 2f are three side elevation views showing an absorbent pad comprising two superposed layers of absorbent material occupying three possible positions one relative to another;

FIGS. 3a and 4a show a first element of the unit as in FIG. 1, illustrated in two alternative embodiments and viewed in perspective;

Figure 3B:
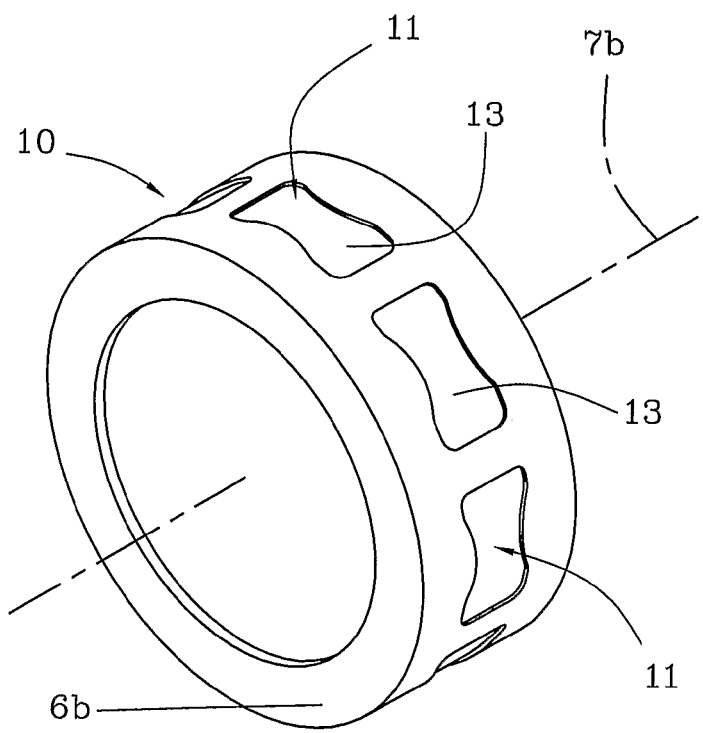
FIGS. 3b and 4b show a second element of the unit as in FIG. 1, illustrated in two alternative embodiments and viewed in perspective.

With reference to FIG. 1, numeral 1 denotes a unit, in its entirety, by means of which to form absorbent multilayer pads 2 (FIGS. 2a ... 2f) for babies' nappies/diapers.

In a preferred though not exclusive configuration, the unit 1 presents a top section comprising a first device 3a and a second device 3b of which the function is to take up, shape and transfer a first layer 4a and a second layer 4b, respectively, of an absorbent material denoted 5.

The first device 3a and the second device 3b appear respectively as a first drum 6a and a second drum 6b located one beside the other and contrarotating about respective parallel axes 7a and 7b. The peripheral surfaces of the first and second drums 6a and 6b rotate tangentially one to another at a transfer station denoted 8.

Numerals 9a and 9b denote conventional infeed stations from which relative streams of absorbent material 5 are directed onto an outer peripheral portion 10 of each drum 6a and 6b.

Figure 4B:
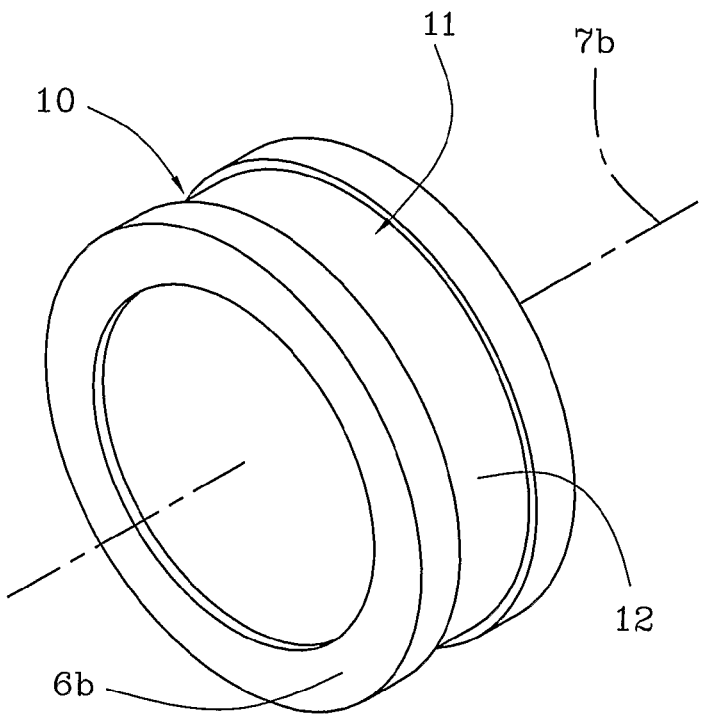

The absorbent material 5 is placed in suitable aspirating recesses 11, which in a first embodiment take the form of a continuous circular channel 12 extending circumferentially around the peripheral portion 10 (FIGS. 4a and 4b). Alternatively, the recesses 11 might consist in a plurality of discrete pockets 13 aligned and equispaced circumferentially around the peripheral portion 10 (FIGS. 3a and 3b).

In both solutions, the recesses 11 are fashioned so as to match the shape of the absorbent pad 2 being manufactured, and able to retain the advancing absorbent material 5 by suction.

In particular, the function of the first drum 6a is to take up, shape and transfer the smaller first layer 4a of absorbent material 5, whilst that of the second drum 6b is to take up, shape and transfer the larger second layer 4b of absorbent material 5.

In practice, absorbent pads 2 for nappies/diapers can be formed by a unit 1 embodied with both drums 6a and 6b presenting recesses 11 of the same geometry (both with continuous channels 12, or both with discrete pockets 13), or with the first drum 6a presenting discrete pockets 13 and the second drum 6b presenting a continuous channel 12. In a preferred embodiment, according to the present invention, the recess 11 of the first drum 6a will present discrete pockets 13, in such a manner that the first layer 4a can be placed in a selected position relative to the second layer 4b.

The absorbent material 5 is transferred by the two rotating drums 6a and 6b from the respective infeed stations 9a to respective release stations 14a and 14b. The release station 14a of the first drum 6a coincides with the transfer station 8 at which the first layer 4a is joined to the second layer 4b.

More exactly, it is at the transfer station 8 that the drums 6a and 6b interface and interact, causing the first layer 4a carried by the first drum 4a to be placed directly over the second layer 4b carried by the second drum 6b. The relative positioning of the two layers 4a and 4b can be varied as required, by coordinating the rotation of the drums 6a and 6b.

Both layers 4a and 4b are therefore retained on the second drum 6b by suction as far as the relative release station 14b, whereupon the same two assembled layers 4a and 4b making up the absorbent pad 2 are directed as one into a compressing station 15 and compacted to form a single core.

The compressing station 15, located thus downstream of the second drum 6b, includes a transport roller 16 disposed tangentially to the selfsame drum 6b at the release station 14b. The roller 16 consequently will rotate in the opposite direction to the drum 6b.

The compressing station 15 further comprises at least one compression element 17, positioned along a peripheral portion of the transport roller 16 and operating in conjunction with the selfsame roller 16, by which the first and second layers 4a and 4b of absorbent material 5 are compacted together to form a one-piece core.

The compression element 17 consists in a pressure roller 19 of small diameter, combining with the outer surface of the transport roller 16 to create a pocket (not illustrated) that can either be contoured to match the shape of the absorbent pad 2 being pressed, or alternatively, devoid of any particular geometry and presenting plain contact surfaces.

With rollers 19 and 16 combining to create a shaped pocket, a uniform force of compression can be applied to the entire pad 2. Advantageously, the pressure roller 19 would have a surface contoured to match the shape of the pad 2, and the transport roller 16 would be plain, thereby allowing the smaller roller 19 to be replaced as necessary with another of different geometry, more easily than the larger roller 16. Alternatively, the surface of the transport roller 16 could be contoured, and the pressure roller 19 left plain.

Where the rollers 19 and 16 combine to create a pocket of no distinct geometry, with plain surfaces, the force of compression is applied non-selectively to the pad 2, with the result that the pad 2 cannot be compacted uniformly.

Before being compressed simultaneously, the two assembled layers 4a and 4b of absorbent material 5 can be enveloped, to advantage, in a protective tissue wrap 20 that will help to ensure a more stable cohesion of the superabsorbent granular material and the fluff pulp.

Preferably, the core layers are sandwiched between two layers of tissue wrap 20, namely a first tissue wrap 20a covering the top part of the pad 2, and a second tissue wrap 20b covering the bottom part.

The first tissue wrap 20a is decoiled from rolls (not illustrated), directed over guide elements 21 and applied immediately downstream of the transfer station 8, straight after the first layer 4a has been joined to the second layer 4b, on the top part of the pad 2 facing away from the second drum 6b.

The second tissue wrap 20b, likewise decoiled from rolls (not illustrated), is applied to the underside of the pad 2 facing away from the transport roller 16 when in rotation, at a point coinciding with the compressing station 15 and marginally preceding the pressure roller 19.

Downstream of the compressing station 15, the unit comprises a sealing and cutting station 22 of familiar type, widely utilized in other devices.

In the event of the second drum 6b presenting a recess 11 with discrete pockets 13, the pads 2 will already be divided up into single pieces, and the sealing unit 22 will simply secure the four edges of the tissue wrap 20.

Where the second drum 6b presents a continuous channel 12, on the other hand, the tissue wrap 20 will be sealed only along two longitudinal edges of the pad 2.

Where the absorbent pad 2 is formed as a continuous web, it must be cut and divided into single pieces.

Accordingly, the area 22a in which the sealing step takes place is followed immediately by an area 22b in which the continuous strip of pad 2 is divided into discrete portions. If the pad 2 is already divided into discrete portions, on the other hand, then only the tissue wrap 20 needs to be cut.

Should the first drum 6a and the second drum 6b be fashioned with pockets 13, these will preferably be spaced closely together so as to minimize waste of the tissue wrap 20.

Downstream of the sealing and cutting station 22, the unit comprises a spacing mechanism 23 of familiar type by which the single pads 2, shaped, cut and faced with tissue wrap 20, are positioned at a given distance one from the next on a belt conveyor 24 that will direct them toward other processing stations downstream of the unit 1.

The spacing mechanism 23 comprises a plurality of carriers 25 revolving around a circular path and controlled by cams 26. The carriers 25 are able to delay the passage of the pads 2 between the sealing and cutting station 22 and the conveyor 24, so that they will be spaced farther apart on the belt. The carriers 23 are then accelerated through the second half of the circular path so as to remain correctly timed with the sealing and cutting station 22 and pick up a further pad 2.

The drawbacks of the prior art are overcome in accordance with the present invention, and the stated objects thus realized.

First and foremost, it will be seen that a unit 1 for forming absorbent pads used in nappies/diapers as described and illustrated combines all the advantages of existing units. The method according to the invention is effective likewise in forming absorbent pads for nappies/diapers, inasmuch as it provides for optimum positioning and faultless compression of the two layers combining to make up a one-piece absorbent core.

Accordingly, greater versatility is afforded by a unit for forming absorbent pads according to the invention than by conventional machines in widespread use. Using a single item of equipment, in effect, assembled layers of absorbent material can be positioned correctly one relative to another and subjected simultaneously to an initial compressing action.

The invention claimed is:

1. A unit for forming multilayer absorbent pads utilized in diapers, comprising:
    a first drum and a second drum by which a respective first layer and second layer of absorbent material are taken up from respective infeed stations, shaped, and transferred to release stations, the first drum and second drum being positioned one alongside the other, contrarotating about two parallel axes and peripherally tangential one to another at a transfer station, the absorbent material being taken up, shaped and transferred by the first and second drums associated and operating in conjunction one with another so as to transfer the first layer directly onto the second layer in a predetermined position coinciding with the transfer station;
    a compressing station positioned downstream of the second drum, the compressing station comprising a transport roller contrarotating tangentially to the second drum, and at least one compression element positioned along a peripheral portion of the transport roller and operating in conjunction with the transport roller to therebetween simultaneously compact the first layer and the second layer of absorbent material together to form a one-piece core.

2. A unit as in claim 1, wherein each of the first and second drums presents an aspirating recess extending along an outer peripheral portion and serving to contain the absorbent material contoured to match the shape of the absorbent pad in production.

3. A unit as in claim 2, wherein the aspirating recess afforded by the first drum presents a transverse dimension less that the transverse dimension of the recess afforded by the second drum, so that the first layer of absorbent material is smaller than the second layer.

4. A unit as in claim 3, wherein the aspirating recess of the first drum includes a continuous circular channel extending circumferentially along the peripheral portion.

5. A unit as in claim 3, wherein the aspirating recess of the second drum includes a continuous circular channel extending circumferentially along the peripheral portion.

6. A unit as in claim 3, wherein the aspirating recess of the first drum includes a plurality of discrete pockets aligned and distributed uniformly and circumferentially along the peripheral portion.

7. A unit as in claim 3, wherein the aspirating recess of the second drum includes a plurality of discrete pockets aligned and distributed uniformly and circumferentially along the peripheral portion.

8. A unit as in claim 1, wherein the compression element comprises a pressure roller combining with the transport roller to create a pocket with contours matched to the shape of the absorbent pad, in such a way that a uniform force of compression is applied to the pad.

9. A unit as in claim 1, wherein the compression element comprises a pressure roller with a plain surface, by which a non-uniform force of compression is applied to the absorbent pad.

10. A unit as in claim 1, and further comprising a device for enveloping together the first and second layers of absorbent material forming the absorbent pad in at least one protective tissue wrap.

11. A unit as in claim 1, comprising a sealing and cutting station located downstream of the compressing station.

12. A unit as in claim 11, comprising a spacing mechanism located downstream of the sealing and cutting station, by which the single absorbent pads are taken up and placed on a conveyor.

13. A method of forming multilayer absorbent pads for diapers, including the steps of:
    feeding absorbent material to a first drum and a second drum, the drums located one beside the other and contrarotating about respectively parallel axes,
    forming a respective first layer and second layer of the absorbent material with the drums,
    joining the first layer of absorbent material in a superposed manner to the second layer of absorbent material, and
    compressing the first layer and the second layer of absorbent material simultaneously so as to compact the absorbent pad, the step of joining the first layer of absorbent material in a superposed manner to the second layer of absorbent material including transferring the first layer onto the second layer while the second layer is retained by the second drum,
    wherein the compressing step comprises compressing the first layer and the second layer of absorbent material at a compression station positioned downstream of the second drum, providing the compression station with a transport roller contrarotating tangentially to the second drum at a release station and at least one compression element positioned along a peripheral portion of the transport roller and operating in conjunction with the transport roller to therebetween simultaneously compact the first layer and the second layer of absorbent material together to form a one-piece core.

14. A method as in claim 13, wherein the first layer and the second layer are compressed only after being joined together.

15. A method as in claim 13, wherein the step of feeding absorbent material to the first drum includes directing the material into a continuous channel afforded by a peripheral portion of the first drum.

16. A method as in claim 13, wherein the step of feeding absorbent material to the second drum includes directing the material into a continuous channel afforded by a peripheral portion of the second drum.

17. A method as in claim 13, wherein the step of feeding absorbent material to the first drum includes directing the material into a plurality of discrete pockets distributed uniformly along a peripheral portion of the first drum.

18. A method as in claim 13, wherein the step of feeding absorbent material to the second drum includes directing the material into a plurality of discrete pockets distributed uniformly along a peripheral portion of the second drum.

19. A method as in claim 13, including a further step of enveloping the absorbent pad formed from the first layer and the second layer of absorbent material in at least one tissue wrap before the first layer and the second layer of absorbent material are compressed simultaneously.

* * * * *